United States Patent [19]

Burns et al.

[11] Patent Number: 5,007,416

[45] Date of Patent: Apr. 16, 1991

[54] THERAPEUTIC ANKLE SUPPORT SYSTEM

[76] Inventors: Paul W. Burns, 36 Greco La., Warwick, R.I. 02886; Gary Burns, 512 Old Baptist Rd., North Kingstown, R.I. 02852

[21] Appl. No.: 507,915

[22] Filed: Apr. 12, 1990

[51] Int. Cl.[5] .............................................. A61F 3/00
[52] U.S. Cl. ................................ 128/80 H; 128/399; 128/403; 128/166
[58] Field of Search ...................... 128/80 R, 80 H, 77, 128/85, 89 R, 90, 166, DIG. 20, 83, 399, 402, 403, 594; 623/37

[56] References Cited

U.S. PATENT DOCUMENTS

| | | | |
|---|---|---|---|
| 3,780,537 | 12/1973 | Spencer | 128/399 X |
| 4,055,188 | 10/1977 | Pelton | 128/403 X |
| 4,280,489 | 7/1981 | Johnson, Jr. | 128/166 X |
| 4,905,998 | 3/1990 | Last | 128/402 X |

FOREIGN PATENT DOCUMENTS 8809156 12/1988 Int'l Pat. Institute ............ 128/80 H Primary Examiner—Richard J. Apley
Assistant Examiner—Jennifer L. Doyle

[57] ABSTRACT

An orthopedic splint comprise a pair of arcuately shaped shell members to which are fastened on the interior surface thereof a foam pad and a flexible therapeutic insert in the form of a pad or a bladder that is filled with a gel material. The arrangement is such that when the shell members are fitted about the lower extremity of a leg and the pad or gel bags have been suitably cooled, the entire assembly may be fitted about the lower leg above the ankle and held in place by means of suitable encircling fastener straps and lacing.

5 Claims, 1 Drawing Sheet

U.S. Patent    Apr. 16, 1991    Sheet 1 of 1    5,007,416
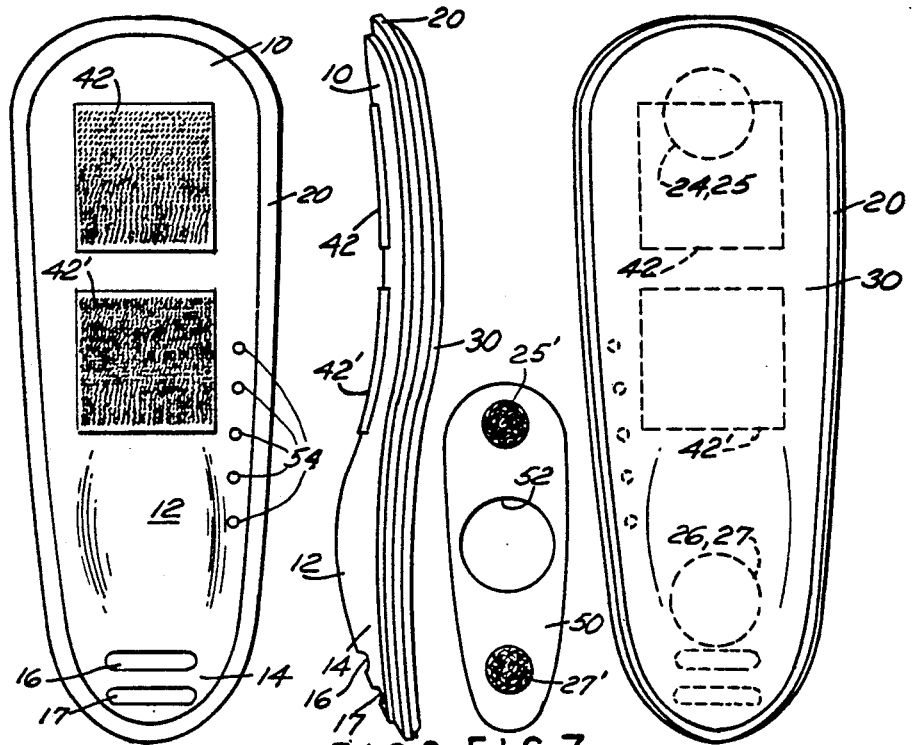
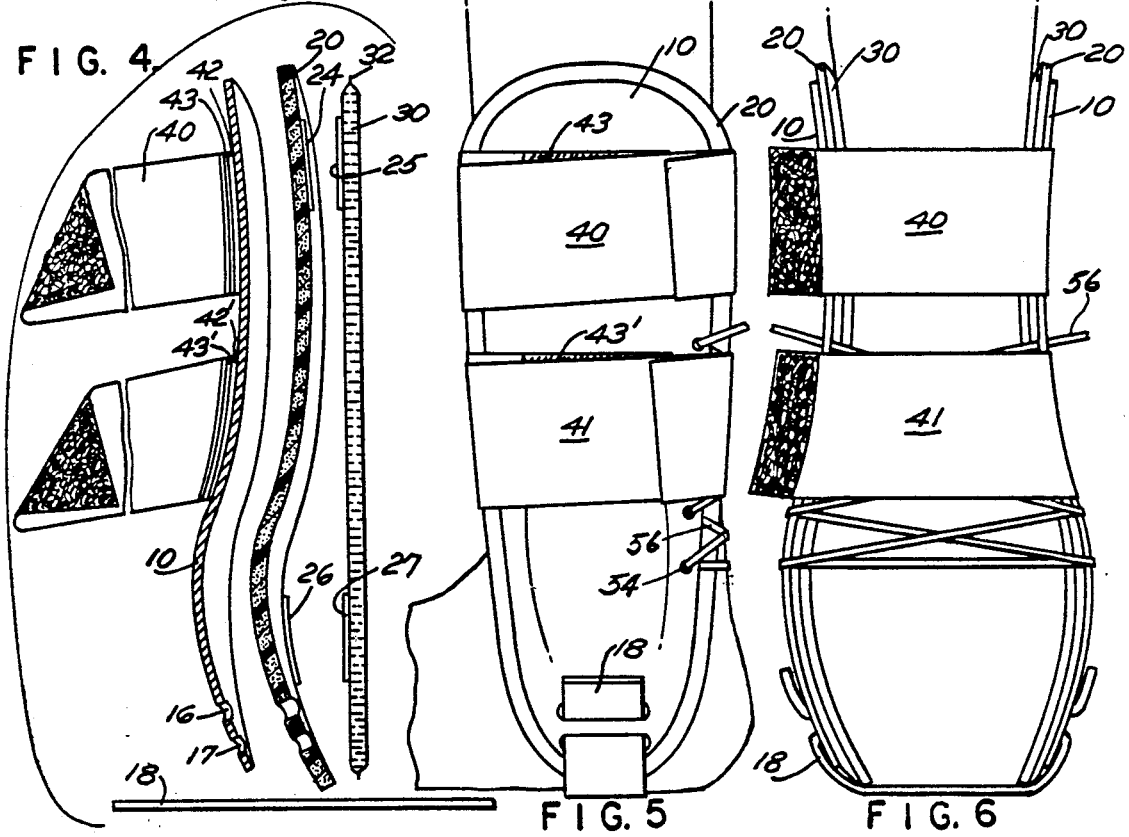

THERAPEUTIC ANKLE SUPPORT SYSTEM

BACKGROUND OF THE INVENTION

Fractures of the limbs, such as the leg, are accompanied by considerable pain and rapid swelling in the area affected. In some cases it is absolutely necessary to, so-called "set" the fracture with a rigid cast and in other cases, the limb need only to be immobilized. It is also important to utilize a form of cooling such as an ice pack in order to reduce the swelling. In the prior art, there are a number of splints and most notably, the splints of the Johnson Pat., U.S. No. 4,280,489 and No. 4,628,945, represent the closest approach to the instant invention.

SUMMARY OF THE INVENTION

The orthopedic splint comprises a pair of rigid semicircular shells that are preferably fabricated from a tough material such as a rigid injection molded polyethylene or polypropylene and each of these shells are provided with a foam inner liner and interiorly of the liner is removably secured a flexible bladder which is substantially coextensive with the shape of the shell and which contains a liquid therapeutic gel within the entire interior thereof. The bottom portion of each of the shells is provided with a pair of slots and fed through the slots are strap means which permit adjustment of the spacing between the shells at the lower end thereof and to secure the shells about a limb are fastener straps provided for encircling the exterior of the shells.

It is a primary object of the present invention to provide an improved orthopedic splint which is not only capable of immobilizing a body part but will also treat the injured portion by applying cooling thereto.

DESCRIPTION OF THE DRAWINGS

FIG. 1 is a side view in elevation of the orthopedic splint according to the present invention;

FIG. 2 is a edge view thereof;

FIG. 3 is an elevational view of the outside surface of one of the orthopedic splints;

FIG. 4 is an exploded view of the one of the orthopedic splints showing each of the major parts separated;

FIG. 5 is a side elevational view partly diagrammatic showing the orthopedic splint fitted about the lower extremity of a foot;

FIG. 6 is a rear view showing the orthopedic splint fitted about the lower extremity; and FIG. 7 is a plan view of an alternate cushion insert.

DESCRIPTION OF THE PREFERRED EMBODIMENT

With reference to the drawings, there is illustrated an orthopedic splint which essentially comprises a pair of substantially identical semicircular shells 10 which are preferably made of a stiff, molded plastic material such as polyethylene that is generally formed and shaped to conform especially to the lateral sides of the lower extremity of a limb. To this extent, the lower portion of the shell is formed with a concavity 12 which, as seen in FIG. 2, is an outwardly bulged area so that the same may accommodate itself about the ankle. The bottom end 14 of the shell is provided with a pair of slots 16, 17 and as seen more particularly in FIGS. 5 and 6, a strap 18 which may be formed of a braided nylon material or woven material is suitably threaded through the slots 16 and 17 to form a bottom fastener. As seen more particularly in FIG. 2 and 4, the shells are somewhat arcuately formed in transverse section and on the inner wall thereof, there is fastened a foam pad 20 which is shaped and sized to overlie the periphery of the shell 10. The layer 20 may be made of any commercially available material and the preferred material is a closed cell polyethylene foam. We have found that it is appropriate to have the shell members of a thickness of approximately 2.3 mm, a longitudinal length of approximately 250 mm and a width of about 75 mm while the foam pad 20 will have a thickness of approximately 5 mm.

As will be apparent from viewing FIG. 4, the foam pad 20 is suitably secured to the inner face of the shell member and then has secured to the surface thereof at least a pair of patches 24, 26 of hook fabric material sold under the trademark Velcro.

Removably fitted to the foam pad by the patches 24, 26 is a closed bladder 30 which has secured to one of the surfaces thereof a mating eye fabric patch 25, 27. The bladder 30 is composed of a pair of thin sheets of suitable flexible plastic material such as a medical grade satin PVC plastic which are secured along its peripheral edges 32 by specially designed high frequency ultra sonic sealing equipment which allows the entrapment of gasses in the bladder while injecting the liquid therapeutic gel therein. Within the interior of the bladder, therefore, is a therapeutic liquid gel material which has the ability to retain a condition, such as a cold condition, by placing the same in a freezer, or in heated water to retain a heated condition above body temperature, for example. The material can be manufactured in accordance with the disclosure in U.S. Pat. Nos. 3,545,230 and/or 3,885,403 and as can be readily seen, the bladder 30 can be removed from the assembly, placed in the freezer and cooled, or placed in hot water and heated, so that a therapeutic effect may be had by the patient wearing the same.

Referring now to FIGS. 5 and 6, it can be appreciated that the shell members 10 may be fitted, let us say about the lower extremity of a leg, that is about the ankle. The lateral adjustment is made by adjusting the strap 18 and then each of the shell members is brought into snug engagement with the lower leg and fastener straps 40 and 41 may be placed about the outer surface of the shell, circumferentially wound thereabout and suitably tensioned so as to be snug but not uncomfortably tight. The strap members 40 and 41 may be composed and fitted with hook-and-loop fasteners 43, 43' at the end so that adjustment can be readily made by the user and the straps may be secured to the shell 10 by patches of hook fastener material 42, 42'. The outer shell may be made of polypropylene and of a thermoform grade so that the shell may be custom fitted to the patient by the use of a heat gun making minor variations in the shape of the shells 10.

The shell members may have five apertures 54 arranged as seen in FIG. 1, along one edge thereof. When lacing 56 as seen in FIGS. 5 and 6 is passed through the apertures, and the members are oriented as seen in FIG. 5 so that the apertures are to the posterior portion of the leg, additional support in the Achille area is provided and this lacing will also stop rotation of the support brace when applied to the leg.

The orthopedic splint of the present invention facilitates management of lower leg injuries by not only assisting in the immobilization thereof but also in providing therapeutic effect by the utilization of the bladder that is filled with a liquid gel material that can be cooled so as to reduce normal swelling that occurs with injuries.

The ankle support may be worn after healing has occurred and the therapeutic gel bladder removed. To this end a supplemental or auxiliary pad is formed of a closed cell foam with a central cutout 52. The pad 50 is has attachment fasteners 25', 27' that will adhere to the corresponding fasteners 24, 26 on the shell 10.

We claim:

1. Orthopedic splint comprising a pair of rigid arcuately shaped shells, said sheels having a pair of spaced slots at one end thereof, a first flexible foam pad insert having the shape of the shell and substantially coextensive therewith, means securing a first said insert to each said shell, said first insert having first surface fastener patches thereon, a second flexible therapeutic pad insert having second surface fastener patches that releasably engage the surface fastener patches on the first insert, fastener straps for encircling the exterior of the shells when the shells are fitted about a body part.

2. An orthopedic splint as in claim 1 wherein the means securing the first insert are surface fastener patches on the inside surface of the shells which releasably engage fastener patches on the outer surface of the first insert and the foam pad has a shape to overlie all edges of the shell.

3. An orthopedic splint as in claim 1 wherein the body part is the lower leg and a strap is threaded through the slots in the shells, a plurality of spaced apertures being provided along one edge of each of the splint shells and lacing is passed through the apertures which will provide support in the Achille area.

4. An orthopedic splint as in claim 1 wherein the therapeutic pad insert is a flexible bladder.

5. An orthopedic splint as in claim 4 wherein the bladder has a therapeutic gel within the interior thereof.

* * * * *